United States Patent [19]
Basch et al.

[11] Patent Number: 4,784,804
[45] Date of Patent: Nov. 15, 1988

[54] N,N'-BIS(4-AZIDOBENZOYL)CYSTINE

[75] Inventors: Ross S. Basch, New York, N.Y.; Michiel E. Ultee, Belle Mead, N.J.

[73] Assignee: New York University, New York, N.Y.

[21] Appl. No.: 894,469

[22] Filed: Aug. 4, 1986

Related U.S. Application Data

[63] Continuation-in-part of Ser. No. 760,281, Jul. 29, 1985, abandoned.

[51] Int. Cl.$^4$ .............................................. C07C 117/08
[52] U.S. Cl. .................................... 260/349; 436/501
[58] Field of Search ......................................... 260/349

[56] References Cited

U.S. PATENT DOCUMENTS 3,123,621  3/1964  Herring ............................... 260/349
3,681,400  8/1972  Rydh .................................... 260/349
4,554,237  11/1985  Kataoka et al. ................ 260/349 X

OTHER PUBLICATIONS

Zabicky, "The Chemistry of Amides", (1970), p. 101, Interscience Publishers–John Wiley & Sons, London–N.Y.–Sydney.
Nefkens et al.; J.A.C.S., 83, (1961), p. 1263.

*Primary Examiner*—Joseph Paul Brust
*Attorney, Agent, or Firm*—Darby & Darby

[57] ABSTRACT

N,N'-Bis(4-Azidobenzoyl) Cystine useful as photoaffinity labels.

3 Claims, 4 Drawing Sheets

PHOTODECAY SPECTRA OF $(ABC)_2$

N,N'-BIS(4-AZIDOBENZOYL)CYSTINE

This is a continuation-in-part of application Ser. No. 760,281, filed July 29, 1985 now abandoned.

FIELD OF THE INVENTION

The present invention relates to novel compounds useful as photoaffinity labels and more particularly to cleavable, heterobifunctional photoaffinity reagents that incorporate a radioisotope.

BACKGROUND OF THE INVENTION

Photoaffinity labelling has been used for at least 20 years in the identification of specific receptor sites on cell surfaces. Several cell surface receptor sites have been identified by this method; such sites include those for acetylcholine, insulin, glucagon, calmodulin and epidermal growth factors, among others. Heterobifunctional photoaffinity labeling reagents transfer a label to a desired receptor site via the natural ligand for the receptor. The reagent is attached to the ligand in a reaction utilizing one of the two different functional groups of the reagent. Usually, the remaining functional group of the photoaffinity reagent is the photoreactive group which remains inert until activated by light. When the ligand carrying the reagent is introduced to the receptor, a light source is used to activate the photoreactive functional group of the reagent which then covalently binds to the surrounding receptor site. The resulting labelled receptor can then be identified using various well-known detection techniques, depending on the type of label used.

By definition, a heterobifunctional photoaffinity labelling reagent has two different functional groups, one for binding the reagent to a ligand, and the other for binding to the receptor for that ligand. At least the latter functional group is photosensitive. Such a reagent also carriers a detectable label that can be used as a marker for the site where the reagent-bound ligand binds to the ligand's receptor. The reagent should also be cleavable to enable the bound receptor and ligand to be separated, if desired. A cleavable reagent can be separated from the ligand after binding to the receptor. The ligand can then be removed, while the label remains bound to the receptor site.

Two types of photosensitive functional groups are generally available. Azide derivatives and diazo derivatives.

Azide derivatives, such as aryl azido groups, produce nitrenes upon photoactivation. Nitrenes are highly desirable in labelling reactions because they have a half life on the order of $10^{-2}$ to $10^{-4}$ seconds, are highly reactive and non-selective. Diazo derivatives produce reactive carbenes upon photolysis.

Currently available conventional functional groups are used to covalently attach the photoaffinity reagent to amino or sulfhydryl groups of the ligand prior to photoactivation at the receptor site. Disulfide bonds can be provided in the photoaffinity reagent as a functional group to react with available (or added) SH (sulfhydryl or thiol) groups on the ligand. A disulfide exchange reaction covalently binds the photoaffinity reagent to the ligand carrying the SH group. Disulfide bonds make useful functional groups because such a bond can be easily broken under reducing conditions, imparting selective cleavability to the reagent.

It is also desirable to provide a photoaffinity reagent having charged side groups available for solubility of the reagent in aqueous media such as physiological solutions to enable use of the reagent with live cells.

Heterobifunctional photoaffinity labels are very useful in identifying receptor sites, because the labelling is highly specific, and can be achieved directly on intact, live cells under physiological conditions.

Labelling the ligands with radioisotopes is known to facilitate detection and identification of photoaffinity-labelled ligands/receptor complexes. However, some ligands cannot be radiolabelled because they lack suitable reactive groups for attaching the radioactive marker. In addition, some ligands are susceptible to denaturation during the labelling with the radioactive marker and do not bind to their receptor. Incorporating the radioactive marker directly into the heterobifunctional photoaffinity reagent eliminates these problems. See, e.g., Ji and Ji, Analytical Biochemistry, 121, 286–289 (1982) describing the labelling of photoaffinity reagents with reactive radioactive markers such as Na$^{125}$I. However, this technique results in the production of several radioactive reaction products having the marker incorporated at varying points on the reagent, and of varying specific activities which make it difficult to identify the receptor site.

Chong & Hodges (J. of Biological Chemistry, 256 5064–5070 (1981)) synthesized a heterobifunctional photoaffinity reagent utilizing tritiated glycine ([2-$^3$H] glycine) as a reactant. The structure of the Chong & Hodges reagent is shown below:

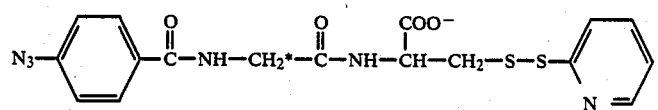

*Denotes radioactivity: in this case one or both glycine hydrogens in the 2-position is $^3$H.

Their purpose was to incorporate the radioactive marker during synthesis of the reagent in order to avoid the problem of variable marker incorporation and variable specific activity. However, tritium has a low specific activity [30–60 Ci/mmol] and is counted with less than 50% efficiency by scintillation counting. Therefore, it is difficult to detect in receptor site identification. Thus, while Chong & Hodges solved one problem, they created another.

Synthesis routes for heterobifunctional photoaffinity reagents are usually multistep and produce a low yield of the desired product.

Although reagents exist that have the three features referred to above, e.g. an aryl azido group, a disulfide bond, and charged groups for aqueous solubility (see Chong and Hodges, J. of Biological Chemistry, 256 5064–5070 (1981)), before the present invention there were no photoaffinity reagents that combined these features and additionally incorporated a radioactive marker of high specific activity. Nor were there any such reagents that could be synthesized easily and inexpensively in a single step with high yield.

It is an object of the present invention to provide a radioactive, cleavable, heterobifunctional photoaffinity reagent that can be prepared inexpensively and with high yield in a one-step synthesis from readily available starting materials.

It is another object of the present invention to provide a radiactive, cleavable, heterobifunctional photoaffinity reagent prepared with a radioisotope of high specific activity.

These and other objects of the invention will become apparent to those skilled in the art from the following detailed description of the invention, the accompanying claims and the appended drawings.

SUMMARY OF THE INVENTION

The present invention is directed to compounds of the formula:

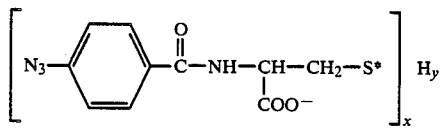

wherein x is 1 or 2; y is 1, when x=1 and zero when x=2; and salt forms thereof. These compounds are useful as a photoaffinity labelling reagent.

The present invention is also directed to a method for synthesizing the above compounds from $^{35}$S-cystine and N-hydroxysuccinimidyl-4-azidobenzoate and to methods and techniques for labelling proteins and cell receptors using the above compound or conjugates of the above compound with proteins or polypeptides ligands.

DETAILED DESCRIPTION OF THE INVENTION

It has been unexpectedly and surprisingly discovered that a radioactive, cleavable, heterobifunctional photoaffinity reagent can be prepared inexpensively and with high yield from readily available starting materials in a single step synthesis. The compound, N-N'-Bis(4-azidobenzoyl)cystine, (ABC)$_2$, is synthesized from N-hydroxysuccinimidyl-4-azidobenzoate (HSAB) and $^{35}$S-cystine in a single step synthesis. The compound ABC$_2$, i.e. 4-azidobenzoyl cystine, is also synthesized, but this compound readily reacts with a second molecule of HSAB to form (ABC)$_2$.

The overall reaction sequence showing preparation of (ABC)$_2$ from $^{35}$S-cystine and HSAB is shown below:

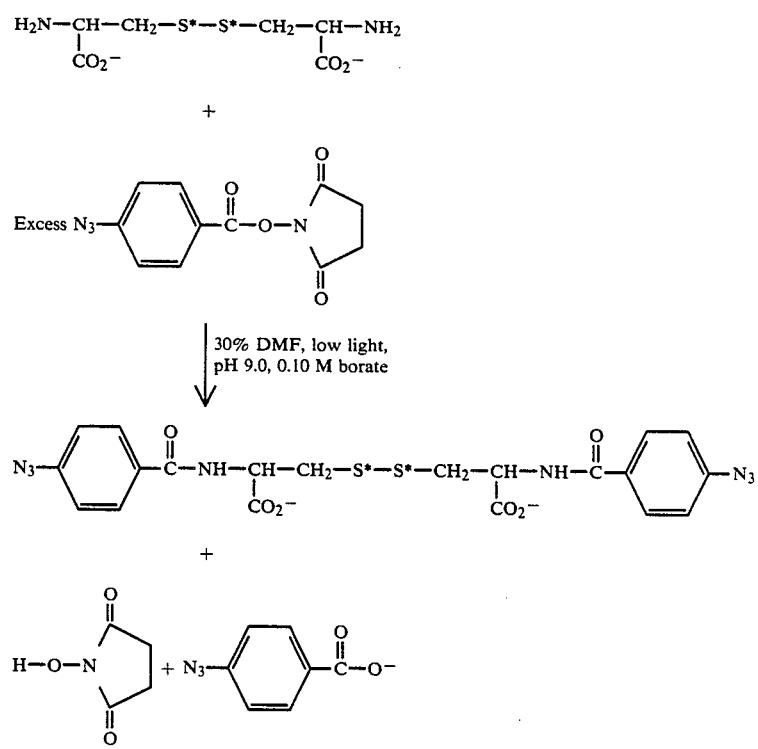

The reaction byproducts are N-hydroxysuccinimide (HS) and azidobenzoate (AB).

The heterobifunctionality of (ABC)$_2$ resides in having two different reactive groups: a disulfide coupling group and an azide photosensitive group. The disulfide coupling group requires free SH groups on the ligand in order to covalently bind to the ligand via a disulfide exchange reaction. Because (ABC)$_2$ couples to free SH groups, protein ligands lacking thiol groups but having disulfide groups must be reduced prior to reaction with (ABC)$_2$.

(ABC)$_2$ is a polar, water-soluble compound that can be covalently coupled to protein and other ligands under mild conditions using a disulfide exchange reaction. After the secondary photo-labelling step has taken place at the receptor site, analysis of the labelled receptor material can be simplified by splitting off the ligand by reducing the disulfide bond between the label and ligand, thus leaving the radioactive label with the labelled receptor.

The following example shows a procedure for the single step synthesis of (ABC)$_2$.

EXAMPLE 1

Cystine (46.2 mg, 0.192 mol), (obtained from Baker Chemical Co., Phillipsburg, N.J.) was dissolved in 210 ml of freshly made 0.2M sodium borate buffer of 30% v/v dimethylformamide (DMF), (obtained from Aldrich Chemical Co., Milwaukee, WI), at a pH of 10. Sulfur-35 labelled cystine (0.592 mCi, $2.19 \times 10^{-6}$ mmol) (obtained from New England Nuclear, Boston, MA) was added to provide trace labeling of the sulfur. The pH was adjusted to 9.0 with 6M HCl and 1.3 ml of DMF. N-hydroxysuccinimidyl azidobenzoate (HSAB), (600 mg, 2.31 mmol) (obtained from Pierce Chem. Co., Rockford, IL) was dissolved in 10.0 ml of DMF. All operations with (ABC)$_2$ or HSAB were performed under dim lighting and in amber glass vials to minimize possible photodecomposition of the aryl azides. One ml of the HSAB solution and 0.43 ml of distilled water were added to the stirred cystine solution every 15 min. The pH was maintained at 9.0 with NaOH. Aliquots of the reaction solution were removed for analysis by thin layer chromatography.

Figure 1:
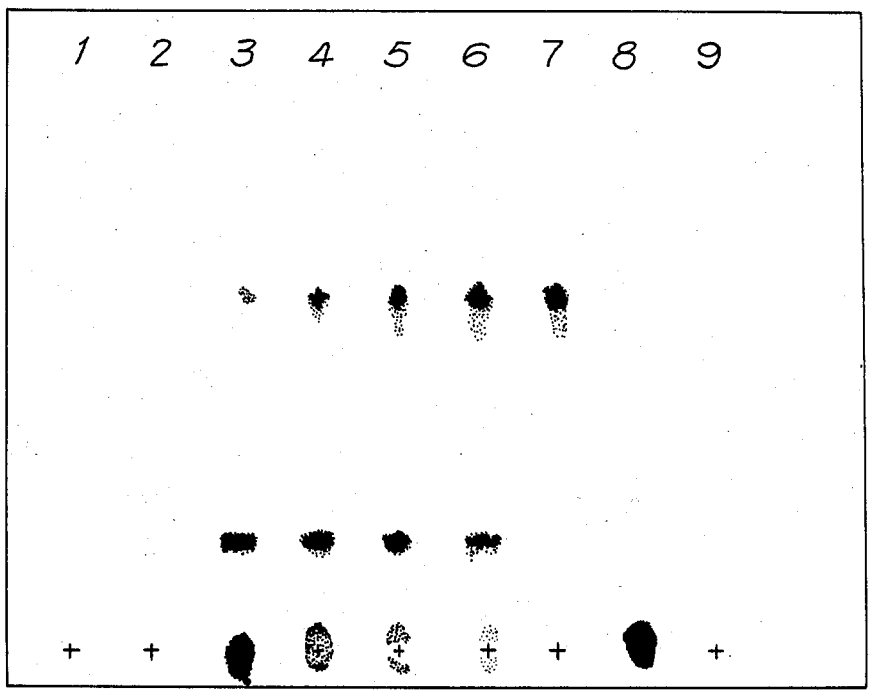
FIG. 1 shows a representative thin layer chromatography plate used to monitor the synthesis reaction of the present compounds.

The reaction solution was evaporated to dryness at 40° C. under reduced pressure in a light-shielded flask. The dry residue was dissolved in 40 ml of distilled water and the solution extracted four times with 10 ml benzene to remove an unidentified non-radioactive by-product. The extraction was monitored by thin layer chromatography. A representative TLC plate used to monitor the reaction is shown in FIG. 1.

Cystine (CC) does not migrate in the solvent system used, and appears as a dark autoradiogram spot at the origin, shown in track 8. Tracks 3–7 show the effect of adding increasing amounts of HSAB to the CC. Cystine gradually decreases while two new radioactive materials form. The first of these to appear moves slightly into the adsorbent layer, and decreases when increasing amounts of HSAB are added. The second product moves about halfway up the plate and first appears when the HSAB:CC ratio is 4:1 (track 4). It gradually increases until, at the 20:1 ratio, it is the only radioactive material (track 7).

It is believed that the first product is cystine with only one amino group substituted by azidobenzoate. This monoadduct, having lost one positively charged amino group, would be expected to migrate somewhat into the TLC adsorbent and is an expected reaction intermediate. It does disappear at high ratios of HSAB:CC. The second product was identified as (ABC)$_2$.

The aqueous solution was acidified with 6M HCl until no more precipitation occurred (approximately 0.1M HCl). The suspension was extracted with 20 ml portions of ether until no further radioactivity was extracted. The ether extracts were pooled and evaporated to dryness in the flash evaporator. The dried residue was dissolved in 9 ml of 10 mM NH$_4$HCO$_3$ (ammonium bicarbonate) and the pH adjusted to 8.4 with NH$_4$OH. This solution was diluted with enough distilled water (42 ml) to reduce the conductivity to that of 50 mM NH$_4$HCO$_3$ (3.7 mS—milli Siemans).

Figure 2:
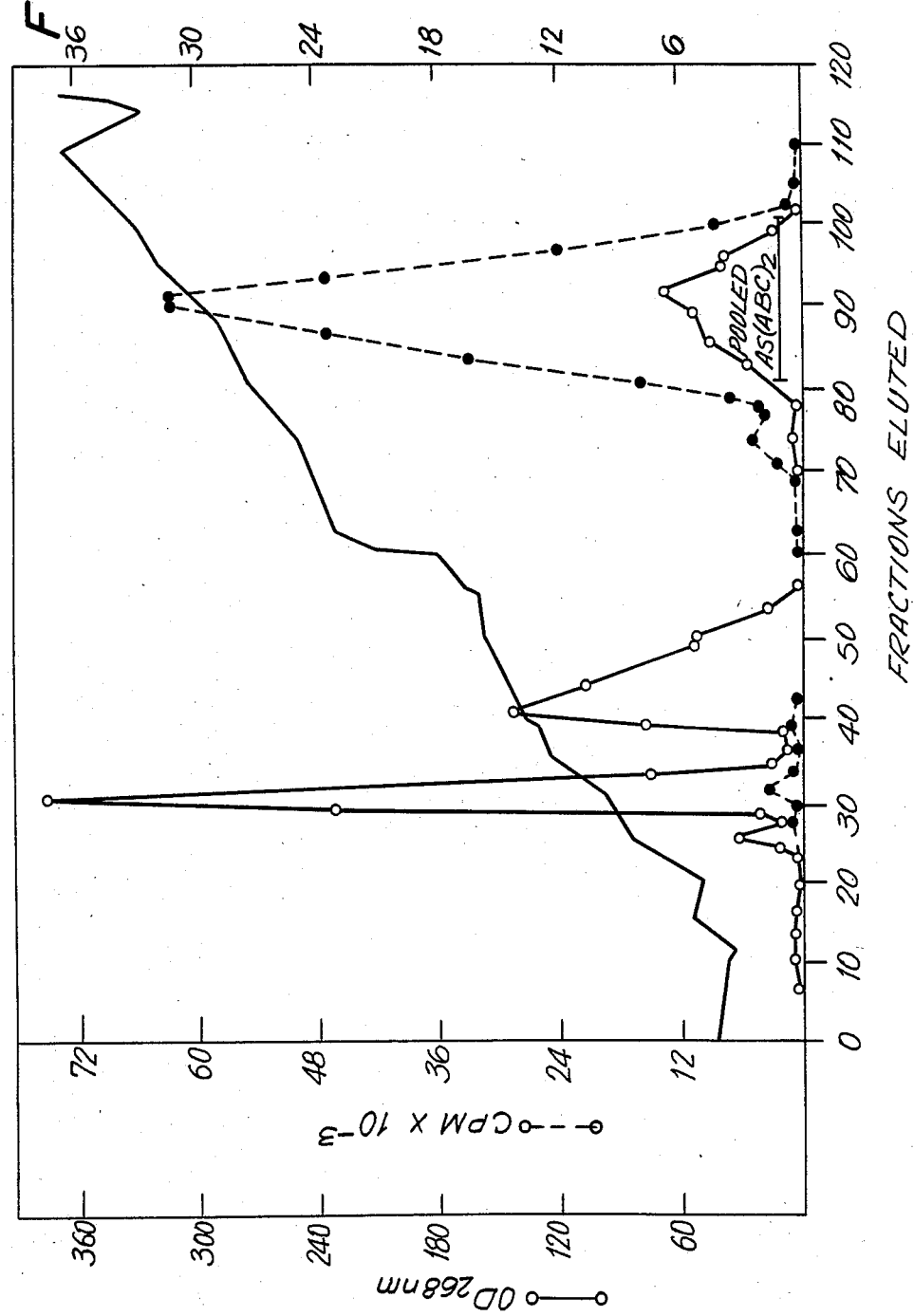
FIG. 2 shows UV absorbance, radioactivity and conductivity of the product of DEAE-Sephadex chromatography containing the reaction product of the present invention.

The aqueous solution was applied to a $1.5 \times 18$ cm column of DEAE-Sephadex A-25 equilibrated in 50 mM NH$_4$HCO$_3$. The column was washed with 80 ml of 50 mM NH$_4$HCO$_3$, and eluted with a linear gradient of 50–600 mM NH$_4$HCO$_3$ (450 ml/side, 70 ml/hr). Fractions (8 ml each) were monitored by scintillation counting, UV absorbance at 268 nm, and conductivity. The results are shown in FIG. 2. The last peak (at approximately fraction 90) eluted from the column contained almost all of the radioactivity. The eluate (from fractions 81–101) was pooled and lyophilized to yield 108 m (57%) of the ammonium salt of (ABC)$_2$. The resulting solid was homogeneous by thin layer chromatography in three solvents (1) acetone:chloroform:acetic acid, 2:2:1; (2) methanol:benzene+acetic acid, 1:1+1%; (3) 6% 2-propanol in benzene and gave a UV spectrum characteristic of phenyl azide.

Figure 3:
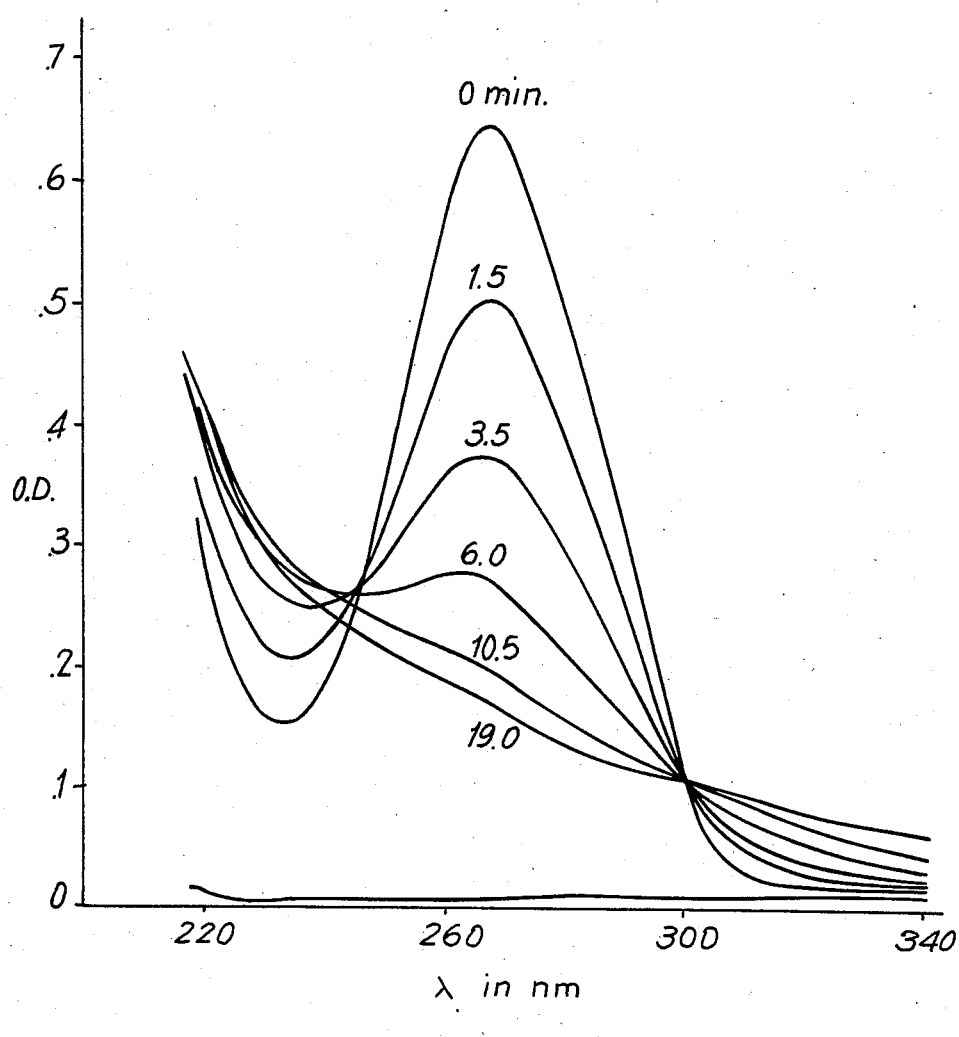
FIG. 3 shows photodecay spectra of the products of the present invention.

In FIG. 3, the solution of (ABC)$_2$ in 50 mM NH$_4$HCO$_3$ was put in a $10 \times 4$ mm quartz cuvette and the spectrum taken. Then it was irradiated with increasing doses of UV light for the times shown, taking a new spectrum after each irradiation. The baseline shown represents the absorbance of the sample cuvette filled with buffer alone.

Further analyses of (ABC)$_2$ were done on its free acid rather than salt form. A portion of the ammonium salt of (ABC)$_2$ was acidified with 50 mM HCl and crystallized from distilled water:2-propanol (1:1) to give purified acid-form (ABC)$_2$ (yield 50%). It was homogeneous by thin layer chromatography and gave the same UV spectrum as the ammonium salt. Mass spectra were obtained by The Rockefeller University Mass Spectrometric Biotechnology Research Resource using a $^{252}$Cf Fission-Fragment Ionization machine built by the university. The parent m/e peak at 531 (M+H), and sodium ion adducts at 553 (M+Na) and 576 (M+2Na), matched the expected molecular weight of 530. Other m/e peaks at 525, 413, 393, 265, 226, 219, 184, 165, 147, 146, 120 and 118 could be accounted for by expected fragments of the (ABC)$_2$ molecule. Elemental analyses were performed by Schwarzkopf Microanalytical Laboratory, Woodside, NY., according to the standard methods. Calculated for $C_{20}H_{18}N_8O_6S_2$: C, 45.28; H, 3.40; N, 21.13. Found: C, 46.55; H, 4.06; N, 19.74.

EXAMPLE 2

Synthesis of high specific activity (ABC)$_2$ $^{35}$S-Cystine (1.0 mCi (milli Curie), 2.49 nm (nanomole)) in 1.1 ml of dilute HCl:ethanol, (9:1) pH 2, was mixed with 246 nm of cystine in 0.10 ml water and the solution lyophilized. The resulting residue (179 nm) was dissolved in 0.19 ml of pH 9.0 0.2M sodium borate and 0.082 ml of DMF was added. The pH was adjusted to 9.0 with small amounts of 1M HCl and NaOH. HSAB in DMF (300 nm/µl) was added with stirring in four 10 µl aliquots every 15 min. The pH was held at 9.0 with aliquots of 1M NaOH, and after six hr. the reaction was deemed complete as assayed by thin layer chromatography.

The (ABC)$_2$ was purified by preparative thin layer chromatography on 20×20 cm PK4F 500$\mu$ plates (Whatman, Clifton, N.J.). The crude reaction mixture was spotted along a line 2 cm from the bottom of the plate. Plates were developed using methanol:benzene (1:1) containing 1% acetic acid. Nearly all the radioactivity, as assayed by autoradiography with Kodak XAR-5 film, was in one band of Rf=0.50. This was well separated from the one other radioactive band (Rf=0.39), as well as from five other bands seen by UV fluorescence inhibition. The silica gel containing the major radioactive band was scraped into a 1.5×10 cm glass chromatography column and the band eluted with 2% acetic acid in 95% ethanol. The eluate contained 47.8 nm (27%) of product that was homogeneous on thin layer chromatography and moved identically to authentic (ABC)$_2$. UV spectra were also the same. The specific activity was 4.90×10$^6$ cpm/nm (2.45 Ci/mmole).

EXAMPLE 3

The procedure of Example 2 was used to produce (ABC)$_2$ from $^{35}$S-cystine of the highest specific activity available. No non-radioactive cystine was added in the procedure. The product had a specific activity of 530 Ci/mmole.

EXAMPLE 4

Preparation of Ligand

Ribonuclease (RNase, from Sigma Chemical Co., St. Louis, MO) (3.0 mg, 0.22 $\mu$mol) in 130 $\mu$l of 0.2M sodium phosphate, pH 6.4, was mixed with dithiothreitol (DTT) (1.35 mg, 8.76 $\mu$mol) and 325 $\mu$l of a buffer containing 0.20M acetic acid, 8M urea, and adjusted to pH 8.6 with concentrated NH$_4$OH. Urea (96 mg) was added to bring the concentration up to 8M, and about 5 $\mu$l of concentrated NH$_4$OH was added to bring the pH to 8.6. After a reaction time of 2-4 hrs. at room temperature, the mixture was acidified to pH 3 with 6M HCl and applied to a 1.0×19 cm column of G-25 Sephadex (Pharmacia, Piscataway, N.J.) equilibrated in 0.2M acetic acid. Fractions of 0.58 ml were collected at 5-6 ml/hr and assayed for UV absorbance at 280 nm and thiol content by reaction with 4-dipyridyl disulfide (Grassetti and Murray, Arch. of Biochem. Biophys. 119, 41-49 (1967)). The protein eluted in the void volume, was well-separated from the excess DTT, and fully reduced in terms of thiol groups. The reduced protein was then used in the coupling reaction with (ABC)$_2$ as soon as possible to avoid air oxidation of the thiol groups.

EXAMPLE 5

The procedure of Example 4 was followed to reduce bovine serum albumin (BSA) instead of ribonuclease. The product was used to test the coupling ability of the compound of the present invention.

EXAMPLE 6

Coupling of (ABC)$_2$ to thiol-containing proteins

Reduced RNase from Example 4 (0.35 mg, 25 nm) in 375 $\mu$l of 0.2M acetic acid was added to (ABC)$_2$ (1.08 mg, 2040 nm), and urea (192 mg, 3.2 mm) added to bring the urea concentration to 8M. The molar amount of (ABC)$_2$ used was ten times the molar amount of protein thiol groups. The volume was increased with 350 $\mu$l of 8M urea, 0.2M NH$_4$CH$_3$CO$_2$ pH 8.4 buffer, and the pH adjusted to 8.5-8.6 with concentrated NH$_4$OH. The reaction mixture was left overnight at room temperature.

The solution was acidified to pH 3.0 and applied to a 1.0×19 cm column of Sephadex G25-40 equilibrated in 0.2M acetic acid. One ml of 8M urea, 0.2M NH$_4$CH$_3$CO$_2$ (pH 8.4) buffer was applied directly after the sample to minimize absorption of (ABC)$_2$ by the gel. Fractions of 0.58 ml were collected at 5 ml/hr and monitored by both absorbance at 280 nm and scintillation counting. The coupled protein eluted in the void volume, 0.3 column volumes ahead of the (ABC)$_2$ and urea. For RNase, an average of 2.3-2.8 ABC groups per protein were coupled.

EXAMPLE 7

The procedure of Example 6 was followed using reduced bovine serum albumin from Example 5 instead of RNase. An average of 11-12 ABC groups per protein were coupled.

EXAMPLE 8

The procedure of Example 6 was followed using chicken ovalbumin (OA) instead of RNase. An average of 2.2-2.5 ABC groups per protein were coupled.

Examples 6, 7 and 8 utilize the conventional functional group of (ABC)$_2$ (disulfide) in order to couple the label to thiol-containing ligands. After the disulfide exchange reaction, (ABC)$_2$ is split at the disulfide bond forming one free molecule of N-4-azidobenzoyl cystine (ABC). The other ABC moiety is bound at the sulfide to the thiol of the ligand. The protein serves as the thiol and the (ABC)$_2$ as the disulfide, which was present in ten-fold molar excess over the thiol content to drive the equilibrium of the exchange reactions towards formation of the mixed disulfide, ABC-protein product. The three proteins (OA, RNase and BSA) of Examples 6, 7 and 8 were coupled with (ABC)$_2$ to yield ABC-protein conjugates. For reduced RNase and BSA, 30-40% of the thiol groups coupled, while for OA slightly more than half did. The ABC groups were assumed to be covalently attached, since on rechromatography of ABC-BSA through G25 Sephadex the radioactivity remained with the BSA peak. Furthermore, the covalent linkage was shown to be a disulfide bond; when ABC-RNase was first treated with DTT, and then chromatographed as before on G25 Sephadex, the radioactivity was removed from the protein and appeared in the salt peak. Unreduced RNase did not react with (ABC)$_2$, indicating that thiol groups were necessary for the coupling reaction.

UV spectra of the ABC-protein conjugates (FIG. 3B) showed a composite absorption of the ABC groups and that of the protein itself. Upon photolysis, the absorption due to ABC is greatly reduced, leaving only the adsorption of the protein. As the photolysis proceeds, the peak position shifts to a longer wavelength characteristic of the unmodified protein.

(ABC)$_2$ can also be coupled to proteins of live cells. Significant labelling of cell surface proteins occurs under conditions that do not compromise cell viability.

To demonstrate specific labelling of a receptor site by the radioactive protein-ABC conjugate, antibodies to ABC were prepared and labelled with ABC-RNase.

EXAMPLE 9

Preparation of Anti-ABC Monoclonal Antibodies

Ten BALB/c mice (from Jackson Laboratories, Bar Harbor, ME) were injected in the hind footpads and intraperitoneally with a total of 60-80 μg of ABC-OA from Example 8 in PBS emulsified 1:1 with complete Freund's adjuvant (Difco Detroit, MI). Four months later a boost injection of 50 μl of ABC-OA in PBS with incomplete Freund's adjuvant (GIBCO, Grand Island, N.Y.) was given intraperitoneally. Enzyme-linked immunoabsorbent assays (ELISA) using a commercial kit (New England Nuclear) were performed on sera from the mice, using as antigens ovalbumin, BSA, and the ABC conjugates of these proteins. Nine of the ten mice produced antibodies to the ABC groups. The one with the highest titer was reboosted three weeks later and killed three days after reboost to provide the spleen cells used in the fusion.

Standard hybridization techniques were followed as based on the method of Kohler and Milstein (Nature, 256, 495-497 1975). P3U-1 myeloma cells—a line of Balb/c origin having immunoglobulin light chains—were mixed with the spleen cells at 1:4 ratio and fused with 30% polyethylene glycol 1000 (Dow Chemical Midland, MI). Alternatively, NS-1 myeloma cells (from the American Type Culture Collection, Rockville, Md.) or any other nonsecreting myeloma line could have been used. Fused cells were cultured in the standard hypoxanthine-aminopterin-thymidine (HAT) selection medium (Littlefield, Science, 145: 709-710, 1964). Screening was done by ELISA using ABC-BSA as the antigen. Cells from positive colonies were cloned by standard limit dilution techniques at 0.5-1.0 cells/well. Two clones (66-B-2 and 11-4B-1) showing vigorous growth and production of anti-ABC specific antibody were expanded to yield about 2 L each of antibody containing media supernatant.

The antibodies were isolated by absorption on Protein-A Sepharose, using the procedure of Ey et al. Immunochemistry, 15, 429-436 (1978). A major $IgG_1$-containing peak eluted between pH 6.5 and 5.5 in each case. On analysis by SDS-PAGE, this material contained only one major band with an apparent molecular weight of 150,000 daltons. By ELISA, both antibodies showed binding to ABC-OA and to ABC-BSA, but not to OA, BSA, or DNP-BSA.

EXAMPLE 10

Photoaffinity labelling of anti-ABC antibodies with ABC-RNase

In each of three quartz fluorescence cuvettes was placed 250 μl of a solution of ABC-RNase (2.85 nm) from Example 6 in 0.20M acetic acid freshly neutralized to pH 7.6 with $NH_4OH$. Anti-ABC monoclonal antibody 66-B-2 from Example 9 was added to the first cuvette, 11-4-B-1 to the second, and the control antibody 2H8 (or normal mouse IgG) to the third. In each case, 0.48 nm of antibody was added in 250 μl of PBS with stirring by a small magnetic stirring bar. An aliquot was removed from each cuvette and set aside as the unirradiated sample. Each cuvette was irradiated for six minutes by positioning it on a magnetic stirrer 1.0 cm away from a short-wavelength UV light. Aliquots were removed from each cuvette after two minutes and the photolysis continued as before.

EXAMPLE 11

Analysis of Photolyzed Material by SDS-PAGE

Standard procedures for SDS-PAGE were carried out with 1.5 mm thick slab gels, 14×27 cm, containing a 5-15% or 9-15% acrylamide gradient and a 4.7% stacking gel. Gels were run at 80-85 V for 12-14 hr, or until the bromophenol blue tracking dye traveled about 15 cm. Samples from Example 10 were first prepared by mixing with 1-2 parts of a pH 6.8 buffer of 0.94% Tris-HCl, 25% glycerol, and 5% SDS. Those that were to be reduced were mixed with 5% V/V of 1.0M DTT and heated in an 85° C. water bath for 5 min. After adding a small amount of bromophenol blue tracking dye to each, the samples were applied to the stacking gel tracks in volumes of 100 μl or less.

After electrophoresis, the gels were stained using a solution of 0.1% Coumassie Brilliant Blue R-250 (from Bio-Red Laboratories, Richmond, CA.) in an aqueous solution containing 50% methanol and 10% acetic acid, again following standard procedures. Destaining was carried out using the same solution without the dye. The gels were then placed in $EN^3$hance solution (New England Nuclear) for 1 hr, followed by a water rinse for 1 hr. They were then dried onto thick filter paper with a gel drier (FIG. 4A). Autoradiograms were made by overlaying the dried gel with Kodak XAR-5 film in X-ray film cassettes for varying lengths of time. Loaded cassettes were stored at −70° C. (FIG. 4B)

Figure 4:
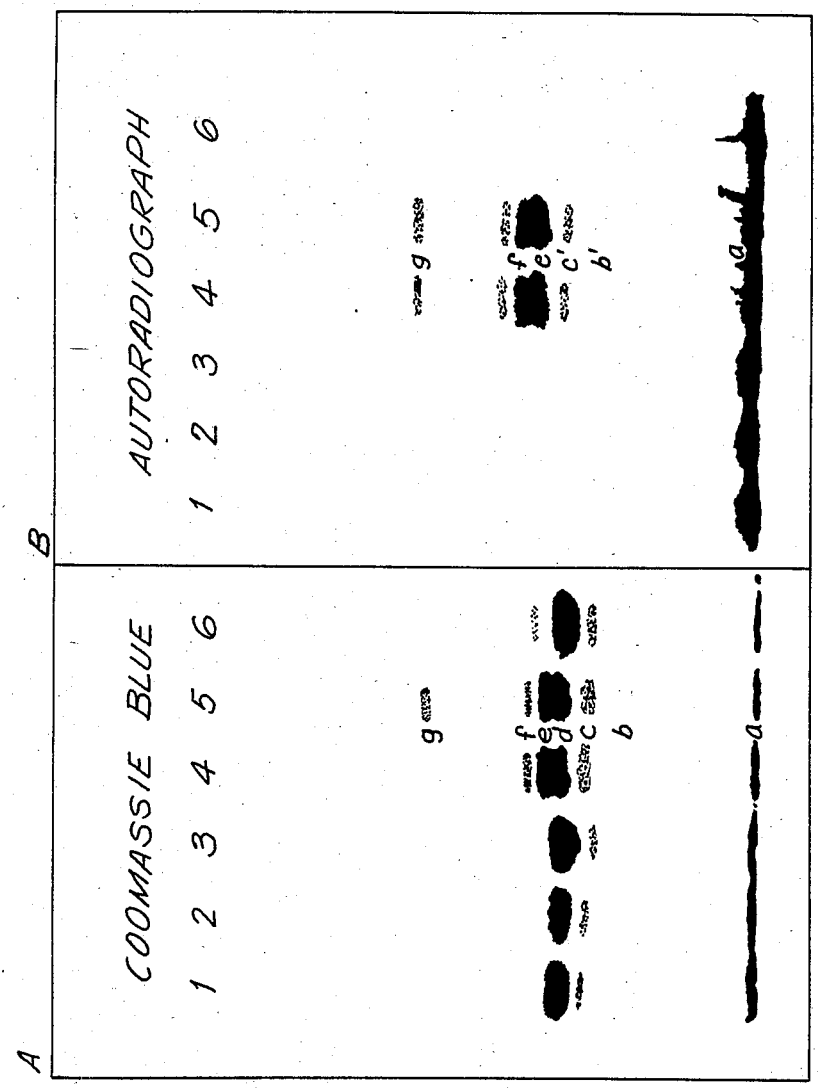
FIG. 4 shows an autoradiograph of SDS-PAGE and a Coumassie blue stain filter paper of antibodies labelled with the product of the present invention.

The SDS-PAGE analysis is shown in FIG. 4. Without UV irradiation (0 min.), the mixtures of ABC-RNase with anti-ABC antibodies (1 and 2) or control antibody (3) are separated by the SDS-PAGE into bands for antibody (d) and RNase (a), as expected. All the radioactivity lies with the RNase band. After 2-6 minutes of photolysis, the pattern radically changes for the anti-ABC antibodies. Both the Coomassie stain and the autoradiogram show new bands (e, f and g) of higher molecular weight than antibody (d). Band e has only slightly higher molecular weight, and is probably the complex of one antibody and one RNase. Band f is again of slightly higher molecular weight, and probably represents two RNase molecules bound to one antibody. Evidence for this assignment comes from both the molecular weight and the relative intensity of the e and f bands in the Coomassie stain compared to the autoradiogram. The apparent specific activity of band f is greater than that of band e. An antibody coupled to two RNase molecules would have twice the radioactivity of one coupled with one RNase molecule. Since RNase has less than 1/10 the molecular weight of an immunoglobulin molecule, the antibody with the two RNase molecules would not have significantly more protein. The faint doublet band (g) may represent higher complexes of antibody RNase molecules. Six minutes of photolysis had about the same effect as two. No labelling was seen of the control antibody (track 6). As expected, RNase was heavily labelled, since ABC-RNase was present in six-fold molar excess over the antibody.

The invention is further described in the accompanying claims.

What is claimed is:

1. A compound of the formula:

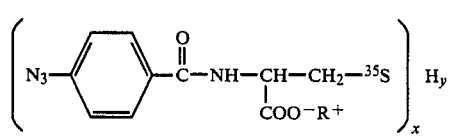

wherein x is 1 or 2; y is 1 when x is 1 and y is zero when x is 2; R is $H^+$ or monovalent cation which appended to the $COO^-$ group forms a water-soluble salt; and $^{35}S$ signifies the radioactive sulfur isotope sulfur $-35$.

2. The compound of claim 1 wherein R is $H^+$.
3. The compound of claim 1 wherein R is $NH_4^+$.

* * * * *

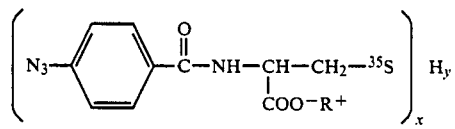

wherein x is 1 or 2; y is 1 when x is 1 and y is zero when x is 2; R is $H^+$ or monovalent cation which appended to the $COO^-$ group forms a water-soluble salt; and $^{35}S$ signifies the radioactive sulfur isotope sulfur $-35$.

2. The compound of claim 1 wherein R is $H^+$.
3. The compound of claim 1 wherein R is $NH_4^+$.

* * * * *